United States Patent
Sydora

(10) Patent No.: US 11,718,573 B2
(45) Date of Patent: Aug. 8, 2023

(54) HEAVY OLIGOMER COMPOSITIONS OF A SELECTIVE 1-HEXENE AND 1-OCTENE CATALYST

(71) Applicant: Chevron Phillips Chemical Company LP, The Woodlands, TX (US)

(72) Inventor: Orson L. Sydora, Sugar Land, TX (US)

(73) Assignee: Chevron Phillips Chemical Company, LP, The Woodlands, TX (US)

( * ) Notice: Subject to any disclaimer, the term of this patent is extended or adjusted under 35 U.S.C. 154(b) by 0 days.

(21) Appl. No.: 17/900,933

(22) Filed: Sep. 1, 2022

(65) Prior Publication Data
US 2023/0080682 A1     Mar. 16, 2023

Related U.S. Application Data

(60) Provisional application No. 63/241,121, filed on Sep. 7, 2021.

(51) Int. Cl.
| | | |
|---|---|---|
| *C07C 11/02* | (2006.01) | |
| *C07C 13/10* | (2006.01) | |
| *C07C 13/11* | (2006.01) | |
| *C07C 11/107* | (2006.01) | |

(52) U.S. Cl.
CPC .......... *C07C 11/02* (2013.01); *C07C 11/107* (2013.01); *C07C 13/10* (2013.01); *C07C 13/11* (2013.01)

(58) Field of Classification Search
None
See application file for complete search history.

(56) References Cited

U.S. PATENT DOCUMENTS

| | | | |
|---|---|---|---|
| 9,969,659 B2 | 5/2018 | Lee | |
| 10,435,336 B2 | 10/2019 | Kreischer | |
| 2018/0016204 A1* | 1/2018 | Coffin | C10M 107/10 |

FOREIGN PATENT DOCUMENTS

| | | |
|---|---|---|
| WO | 2017011127 A1 | 1/2017 |

OTHER PUBLICATIONS

Zychlinski et al. "Investigations on the Thermal Decomposition of n-Dodecylcyclopentane in the Gas Phase" Journal f. prakt. Chemie. 324, 6, pp. 964-974. 1982 (Year: 1982).*
Carter et al, High Activity Ethylene Trimerization Catalysts Based on Diphoshine Ligands, Chem Commun, 2002, pp. 858-859.
Do, et al, Mechanistic Studies of Ethylene and a-Olefin Co-Oligomerization Catalyzed by Chromium-PNP Complexes, Organometallics, 2012, 31, pp. 5143-5149.
Deckers, et al, Catalytic Trimerization of Ethene with Highly Active Cyclopentadienyl-Arene Titanium Catalysts, Organometallics, 21(23), 2002, pp. 5122-5135.
Suzuki, et al, Trimerization of Ethylene to 1-Hexene with Titanium Complexes, Organometallics, 29(11), 2010, pp. 2394-2396.
Zilbershtein, et al, Decene Formation in Ethylene Trimerization Reaction Catalyzed by Cr-Pyrrole System, Applied Catalysis A, General, 475 (2014) pp. 371-378.
Zhou, et al, Structural Analysis of Isomers in Commercial Alpha-Olefins, Petro Process and Petrochem 36 5 2005 pp. 51-56—English Translation.
International Search Report and the Written Opinion of the International Searching Authority in PCT/US2022/075858 dated Jan. 13, 2023, 13 pages.

* cited by examiner

*Primary Examiner* — In Suk C Bullock
*Assistant Examiner* — Alyssa L Cepluch
(74) *Attorney, Agent, or Firm* — Merchant & Gould P.C.

(57) ABSTRACT

A $C_{10}$ hydrocarbon composition of greater than 55 wt. % $C_{10}$ mono-olefins containing from 11 to 45 wt. % 1-decene, at least 0.5 wt. % 2-butyl-1-hexene, at least 1 wt. % 3-propyl-1-heptene, from 0.5 to 12 wt. % 4-ethyl-1-octene, at least 4 wt. % 4-penten-1-yl-cyclopentane, and from 2 to 40 wt. % 5-methyl-1-nonene. A $C_{12}$ hydrocarbon composition of greater than 60 wt. % $C_{12}$ mono-olefins containing at least 8 wt. % 1-dodecene and at least 0.5 wt. % 6-hepten-1-yl-cyclopentane, and the composition also containing heptylcyclopentane and n-dodecane at a weight ratio of heptylcyclopentane to n-dodecane from 0:3:1 to 8:1. A $C_{14}$ hydrocarbon composition of greater than 60 wt. % $C_{14}$ mono-olefins containing at least 12 wt. % 1-tetradecene and at least 0.5 wt. % 8-nonen-1-yl-cyclopentane, and the composition also containing from 3 to 30 wt. % of n-tetradecane and nonylcyclopentane.

21 Claims, No Drawings

HEAVY OLIGOMER COMPOSITIONS OF A SELECTIVE 1-HEXENE AND 1-OCTENE CATALYST

REFERENCE TO RELATED APPLICATION

This application claims the benefit of U.S. Provisional Patent Application No. 63/241,121, filed on Sep. 7, 2021, the disclosure of which is incorporated herein by reference in its entirety.

FIELD OF THE INVENTION

The present disclosure relates generally to $C_{10}+$ olefins, and more particularly, relates to linear, branched, and cyclic $C_{10}$-$C_{14}$ olefins produced from ethylene oligomerization processes.

BACKGROUND OF THE INVENTION

Many hydrocarbons heavier than 1-octene are produced in ethylene oligomerization processes. However, isolation and identification of various mono-olefins and hydrocarbons in the $C_{10}$-$C_{14}$ range are difficult. It would be beneficial to determine the compositional breakdown of $C_{10}$-$C_{14}$ mono-olefins and hydrocarbons in the oligomer product resulting from ethylene oligomerization processes. Accordingly, it is to these ends that the present invention is generally directed.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Olefin compositions are described herein. A first composition consistent with this disclosure can comprise at least 55 wt. % $C_{10}$ mono-olefins. In the first composition, the $C_{10}$ mono-olefins can comprise from 11 to 45 wt. % 1-decene, at least 0.5 wt. % 2-butyl-1-hexene, at least 1 wt. % 3-propyl-1-heptene, from 0.5 to 12 wt. % 4-ethyl-1-octene, at least 4 wt. % 4-penten-1-yl-cyclopentane, and from 2 to 40 wt. % 5-methyl-1-nonene. As one of skill in the art would readily recognize, the total of these and other components does not exceed 100 wt. %.

A second composition provided herein can comprise at least 60 wt. % $C_{12}$ mono-olefins. In the second composition, the $C_{12}$ mono-olefins can comprise at least 8 wt. % 1-dodecene and at least 0.5 wt. % 6-hepten-1-yl-cyclopentane, and the composition can comprise heptylcyclopentane and n-dodecane at a weight ratio of heptylcyclopentane to n-dodecane from 0:3:1 to 8:1.

A third composition provided herein can comprise at least 60 wt. % $C_{14}$ mono-olefins. In the third composition, the $C_{14}$ mono-olefins can comprise at least 12 wt. % 1-tetradecene and at least 0.5 wt. % 8-nonen-1-yl-cyclopentane, and the composition can comprise a total of from 3 to 30 wt. % of n-tetradecane and nonylcyclopentane.

Also described herein are $C_{10}$-$C_{12}$ compositions, which can comprise generally from 30 to 60 wt. % of the first composition and from 38 to 68 wt. % of the second composition, and $C_{12}$-$C_{14}$ compositions, which can comprise generally from 45 to 85 wt. % of the second composition and from 20 to 50 wt. % of the third composition. Similarly, a $C_{10}$-$C_{14}$ composition consistent with this disclosure often can contain from 25 to 47 wt. % of the first composition, from 30 to 55 wt. % of the second composition, and from 12 to 35 wt. % of the third composition. In like manner, a $C_{10}$-$C_{18}$ composition provided herein can comprise from 15 to 40 wt. % of the first composition, from 19 to 40 wt. % of the second composition, from 7 to 25 wt. % of the third composition, and from 18 to 40 wt. % of $C_{16}$-$C_{18}$ hydrocarbons.

Both the foregoing summary and the following detailed description provide examples and are explanatory only. Accordingly, the foregoing summary and the following detailed description should not be considered to be restrictive. Further, features or variations can be provided in addition to those set forth herein. For example, certain aspects can be directed to various feature combinations and sub-combinations described in the detailed description.

Definitions

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

In this disclosure, while compositions, processes/methods, and systems are described in terms of "comprising" various materials, steps, and components, the compositions, processes/methods, and systems also can "consist essentially of" or "consist of" the various materials, steps, or components, unless stated otherwise. The terms "a," "an," and "the" are intended to include plural alternatives, e.g., at least one, unless otherwise specified.

Generally, groups of elements are indicated using the numbering scheme indicated in the version of the periodic table of elements published in *Chemical and Engineering News*, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; and a general reference to a butyl group includes an n-butyl group, a sec-butyl group, an iso-butyl group, and a t-butyl group.

The terms "contacting" and "combining" are used herein to describe compositions, processes/methods, and systems in which the materials are contacted or combined together in any order, in any manner, and for any length of time, unless otherwise specified. For example, the materials can be blended, mixed, slurried, dissolved, reacted, treated, impregnated, compounded, or otherwise contacted or combined in some other manner or by any suitable method or technique.

The term "hydrocarbon" whenever used in this specification and claims refers to a compound containing only carbon and hydrogen. Other identifiers can be utilized to indicate the presence of particular groups in the hydrocarbon (e.g., halogenated hydrocarbon indicates that the presence of one or more halogen atoms replacing an equivalent number of hydrogen atoms in the hydrocarbon).

The term "alkane" whenever used in this specification and claims refers to a saturated hydrocarbon compound. Other identifiers can be utilized to indicate the presence of particular groups in the alkane (e.g., halogenated alkane indicates that the presence of one or more halogen atoms replacing an equivalent number of hydrogen atoms in the alkane).

The term "olefin" whenever used in this specification and claims refers to hydrocarbons that have at least one carbon-carbon double bond that is not part of an aromatic ring or an aromatic ring system. The term "olefin" includes aliphatic and aromatic, cyclic and acyclic, and/or linear and branched hydrocarbons having at least one carbon-carbon double bond that is not part of an aromatic ring or ring system unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s).

The term "alpha olefin" as used herein refers to any olefin that has a carbon-carbon double bond between the first and second carbon atom of the longest contiguous chain of carbon atoms. The term "alpha olefin" includes linear and branched alpha olefins and alpha olefins which can have more than one non-aromatic carbon-carbon double bond, unless expressly stated otherwise. The term "normal alpha olefin" as used herein refers to a linear aliphatic hydrocarbon mono-olefin having a carbon-carbon double bond between the first and second carbon atoms. The term "linear internal olefin" as used herein refers to a linear aliphatic hydrocarbon mono-olefin having a double bond that is not between the first and second carbon atom.

The term oligomer refers to a product that contains from 2 to 20 monomer units. The terms "oligomerization product" and "oligomer product" include all products made by the "oligomerization" process, including the "oligomers" and products which are not "oligomers" (e.g., products which contain more than 20 monomer units, or solid polymer), but exclude other non-oligomer components of an oligomerization reaction zone effluent stream, such as unreacted ethylene, organic reaction medium, and hydrogen, amongst other components.

Several types of ranges are disclosed in the present invention. When a range of any type is disclosed or claimed, the intent is to disclose or claim individually each possible number that such a range could reasonably encompass, including end points of the range as well as any sub-ranges and combinations of sub-ranges encompassed therein. For example, when a chemical moiety having a certain number of carbon atoms is disclosed or claimed, the intent is to disclose or claim individually every possible number that such a range could encompass, consistent with the disclosure herein. For example, the disclosure that a compound is a $C_1$ to $C_{18}$ hydrocarbon, or in alternative language, a hydrocarbon having from 1 to 18 carbon atoms, as used herein, refers to a compound that can have 1, 2, 3, 4, 5, 6, 7, 8, 9, 10, 11, 12, 13, 14, 15, 16, 17, or 18 carbon atoms, as well as any range between these two numbers (for example, a $C_{10}$ to $C_{14}$ hydrocarbon), and also including any combination of ranges between these two numbers (for example, a $C_2$ to $C_4$ and a $C_{10}$ to $C_{18}$ hydrocarbon). Likewise, all other ranges disclosed herein should be interpreted in a manner similar to this example.

In general, an amount, size, formulation, parameter, range, or other quantity or characteristic is "about" or "approximate" whether or not expressly stated to be such. Whether or not modified by the term "about" or "approximately," the claims include equivalents to the quantities or characteristics.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

The present invention is directed generally to $C_{10}+$ olefins, such as linear, branched, and cyclic $C_{10}$-$C_{14}$ olefins produced from ethylene oligomerization processes. $C_{10}+$ olefins can be produced by contacting ethylene and a chromium-based catalyst system to form an oligomer product containing 1-hexene, 1-octene, and $C_{10}+$ olefins, and subsequently separating or fractionating the oligomer product into $C_6$ olefins such as 1-hexene, $C_8$ olefins such as 1-octene, and $C_{10}+$ olefins.

The $C_{10}+$ olefins can be further separated or fractionated into a $C_{10}$ composition, a $C_{12}$ composition, a $C_{14}$ composition, and $C_{16}$ and/or $C_{18}$ fractions. Any suitable technique can be used, such as vacuum distillation.

General information on chromium-based catalyst systems, ethylene oligomerization processes, and isolation of oligomer product fractions can be found, for instance, in U.S. Pat. Nos. 10,493,422, 10,464,862, and 10,435,336.

$C_{10}$ Compositions

A first composition disclosed herein can comprise at least 55 wt. % $C_{10}$ mono-olefins. In some aspects, the first composition can comprise at least 60 wt. % $C_{10}$ mono-olefins, at least 65 wt. % $C_{10}$ mono-olefins, at least 70 wt. % $C_{10}$ mono-olefins, at least 80 wt. % $C_{10}$ mono-olefins, or at least 85 wt. % $C_{10}$ mono-olefins. Therefore, illustrative and non-limiting ranges for the amount of $C_{10}$ mono-olefins in the composition can include from 55 to 98 wt. %, from 70 to 95 wt. %, from 85 to 95 wt. %, from 55 to 85 wt. %, from 60 to 92 wt. %, or from 65 to 85 wt. %, and the like.

In the first composition, the $C_{10}$ mono-olefins can comprise from 11 to 45 wt. % 1-decene, at least 0.5 wt. % 2-butyl-1-hexene, at least 1 wt. % 3-propyl-1-heptene, from 0.5 to 12 wt. % 4-ethyl-1-octene, at least 4 wt. % 4-penten-1-yl-cyclopentane, and from 2 to 40 wt. % 5-methyl-1-nonene. While not limited thereto, the amount of 1-decene, based on the total $C_{10}$ mono-olefins in the composition, often can range from 12 to 42 wt. %. In one aspect, for example, the $C_{10}$ mono-olefins can contain from 12 to 30 wt. % 1-decene, while in another aspect, from 15 to 38 wt. %, and from 17 to 35 wt. % in yet another aspect, and from 20 to 30 wt. % in still another aspect.

At least 0.5 wt. % of the $C_{10}$ mono-olefins in the first composition can be 2-butyl-1-hexene. Typical ranges for the amount of 2-butyl-1-hexene in the $C_{10}$ mono-olefins include, but are not limited to, from 0.5 to 12 wt. %, from 0.75 to 12 wt. %, from 1 to 8 wt. %, or from 2 to 6 wt. %. Additionally, the $C_{10}$ mono-olefins in the first composition also contain at least 1 wt. % 3-propyl-1-heptene. Based on $C_{10}$ mono-olefins, the amount of 3-propyl-1-heptene can range from 1 to 27 wt. %; alternatively, from 3 to 25 wt. %; alternatively, from 5 to 22 wt. %; or alternatively, from 7 to 17 wt. %. The first composition also can contain from 0.5 to 10 wt. % 4-ethyl-1-octene, based on the $C_{10}$ mono-olefins. For instance, the first composition can contain, based on the $C_{10}$ mono-olefins, from 0.75 to 7 wt. %, from 0.75 to 5 wt. %, from 1 to 5 wt. %, or from 1 to 4 wt. %, of 4-ethyl-1-octene. Further, the first composition can contain at least 4 wt. % 4-penten-1-yl-cyclopentane, with typical ranges for the amount of 4-penten-1-yl-cyclopentane including from 4 to 40 wt. %, from 4 to 37 wt. %, from 5 to 34 wt. %, from 7 to 30 wt. %, or from 10 to 25 wt. %. As above, these weight percentages are based on the amount of $C_{10}$ mono-olefins in the first composition. Lastly, the first composition also can contain, based on $C_{10}$ mono-olefins, from 2 to 40 wt. % 5-methyl-1-nonene. Other suitable ranges for the amount of 5-methyl-1-nonene include, but are not limited to, from 2 to 38 wt. %, from 4 to 40 wt. %, from 4 to 33 wt. %, from 6 to 33 wt. %, or from 10 to 28 wt. %.

In the first composition, the weight ratio of (2-butyl-1-hexene+3-propyl-1-heptene+4-ethyl-1-octene+5-methyl-1-nonene) to 1-decene typically falls within a range from 0.2:1 to 10:1. In one aspect, the ratio is in a range from 0.3:1 to 8:1, while in another aspect, the ratio is in a range from 0.35:1 to 6:1, and in yet another aspect, the ratio is in a range from 0.4:1 to 5:1, and in still another aspect, the ratio is in a range from 0.8:1 to 5:1. Additionally or alternatively, the weight ratio of 4-penten-1-yl-cyclopentane to 1-decene in the first composition often ranges from 0:1:1 to 3:1, such as from 0.2:1 to 2:1, from 0.2:1 to 1.2:1, from 0.3:1 to 1.5:1, from 0.3:1 to 1:1, or from 0.4:1 to 0.9:1. Additionally or alternatively, the weight ratio of (2-butyl-1-hexene+3-propyl-1-heptene+4-ethyl-1-octene+5-methyl-1-nonene) to 4-penten-1-yl-cyclopentane can range from 0.1:1 to 12:1, and more often, can range from 0.4:1 to 10:1, from 4:1 to 10:1, from 6:1 to 9:1, from 0.3:1 to 4:1, or from 0.4:1 to 3:1.

Optionally, the $C_{10}$ mono-olefins in first composition also can further comprise 2-ethyl-1-octene and/or 3-methyl-1-nonene. When present, based on the $C_{10}$ mono-olefins, the first composition can comprise from 0.3 to 8 wt. %, from 0.5 to 5 wt. %, from 1 to 5 wt. %, or from 0.8 to 4 wt. % of 2-ethyl-1-octene. Likewise, when present, the 3-methyl-1-nonene can be present in an amount from greater than 0 to 10 wt. %, from greater than 0 to 8 wt. %, from greater than 0 to 6 wt. %, or from 2 to 7 wt. %, based on $C_{10}$ mono-olefins.

In addition to $C_{10}$ mono-olefins, the first composition also can contain non-olefinic hydrocarbons, such as alkanes like n-decane and pentylcyclopentane. The amount of pentylcyclopentane in the composition can range from 1 to 20 wt. %, from 2 to 18 wt. %, from 3 to 15 wt. %, from 5 to 13 wt. %, or from 7 to 13 wt. %, although not limited thereto. In general, the first composition is predominantly $C_{10}$ hydrocarbons (inclusive of $C_{10}$ mono-olefins), and often the first composition contains at least 90 wt. % $C_{10}$ hydrocarbons, at least 95 wt. % $C_{10}$ hydrocarbons, at least 96 wt. % $C_{10}$ hydrocarbons, at least 97 wt. % $C_{10}$ hydrocarbons, at least 98 wt. % $C_{10}$ hydrocarbons, or at least 99 wt. % $C_{10}$ hydrocarbons.

$C_{12}$ Compositions

A second composition disclosed herein can comprise at least 60 wt. % $C_{12}$ mono-olefins. In some aspects, the second composition can comprise at least 65 wt. % $C_{12}$ mono-olefins, at least 70 wt. % $C_{12}$ mono-olefins, at least 75 wt. % $C_{12}$ mono-olefins, at least 80 wt. % $C_{12}$ mono-olefins, or at least 85 wt. % $C_{12}$ mono-olefins. Therefore, illustrative and non-limiting ranges for the amount of $C_{12}$ mono-olefins in the second composition can include from 60 to 99 wt. %, from 60 to 95 wt. %, from 62 to 97 wt. %, from 70 to 98 wt. %, from 70 to 95 wt. %, from 75 to 95 wt. %, from 80 to 97.5 wt. %, from 80 to 95 wt. %, or from 85 to 99 wt. %, and the like.

In the second composition, the $C_{12}$ mono-olefins can comprise at least 8 wt. % 1-dodecene and at least 0.5 wt. % 6-hepten-1-yl-cyclopentane, and the second composition also can comprise heptylcyclopentane and n-dodecane at a weight ratio of heptylcyclopentane to n-dodecane from 0:3:1 to 8:1. While not limited thereto, the amount of 1-dodecene, based on the total $C_{12}$ mono-olefins in the composition, often can range from 8 to 40 wt. %. In one aspect, for example, the $C_{12}$ mono-olefins can contain from 9 to 35 wt. % 1-dodecene, while in another aspect, from 10 to 33 wt. %, and from 12 to 29 wt. % in yet another aspect, and from 13 to 23 wt. % in still another aspect.

At least 22 wt. % of the $C_{12}$ mono-olefins in the second composition can be non-cyclic branched $C_{12}$ mono-olefins. Representative non-cyclic branched $C_{12}$ mono-olefins can include, but are not limited to, 5-methyl-1-undecene, 7-methyl-1-undecene, 4-ethyl-1-decene, 6-ethyl-1-decene, 3-propyl-1-nonene, 5-propyl-1-nonene, 2-butyl-1-octene, 3-butyl-1-octene, 4-butyl-1-octene, and the like, as well as any combination thereof. In some aspects, from 27 to 90 wt. % of the $C_{12}$ mono-olefins in the second composition are non-cyclic branched $C_{12}$ mono-olefins, such as from 22 to 90 wt. %, from 29 to 88 wt. %, from 60 to 86 wt. %, from 60 to 80 wt. %, from 35 to 85 wt. %, from 33 to 50 wt. %, or from 33 to 40 wt. %, and the like.

At least 0.5 wt. % of the $C_{12}$ mono-olefins in the second composition can be 6-hepten-1-yl-cyclopentane. Typical ranges for the amount of 6-hepten-1-yl-cyclopentane in the $C_{12}$ mono-olefins include, but are not limited to, from 0.5 to 40 wt. %, from 1 to 35 wt. %, from 2 to 40 wt. %, from 2 to 32 wt. %, from 3 to 20 wt. %, or from 4 to 15 wt. %.

In the second composition, the weight ratio of 1-dodecene to 6-hepten-1-yl-cyclopentane typically falls within a range from 0:4:1 to 12:1. In one aspect, the ratio is in a range from 0.6:1 to 10:1, while in another aspect, the ratio is in a range from 0.6:1 to 4:1, and in another aspect, the ratio is in a range from 0.9:1 to 8:1, and in yet another aspect, the ratio is in a range from 0.9:1 to 6:1, and in still another aspect, the ratio is in a range from 1.5:1 to 4:1. Additionally or alternatively, the weight ratio of non-cyclic branched $C_{12}$ mono-olefins to 6-hepten-1-yl-cyclopentane in the second composition often ranges from 0.4:1 to 55:1, such as from 0.6:1 to 50:1, from 15:1 to 45:1, from 30:1 to 45:1, from 0.6:1 to 30:1, from 0.6:1 to 15:1, or from 0.9:1 to 11:1.

In addition to $C_{12}$ mono-olefins, the second composition also can contain non-olefinic hydrocarbons, such as alkanes like heptylcyclopentane and n-dodecane at a weight ratio of heptylcyclopentane to n-dodecane from 0:3:1 to 8:1. While not limited thereto, the amount of n-dodecane in the second composition can range from 0.25 to 18 wt. %, from 0.5 to 16 wt. %, from 0.5 to 10 wt. %, from 0.75 to 8 wt. %, from 1 to 12 wt. %, from 8 to 14 wt. %, or from 0.75 to 10 wt. %. The amount of heptylcyclopentane in the composition can be range from 0.25 to 25 wt. %, from 0.5 to 23 wt. %, from 1 to 23 wt. %, from 3 to 20 wt. %, from 1 to 18 wt. %, or from 3 to 10 wt. %, although not limited thereto. The weight ratio of heptylcyclopentane to n-dodecane can vary from 0:3:1 to 8:1, and other suitable range include, but are not limited to, from 0:3:1 to 6:1, from 0.3:1 to 3:1, from 0.5:1 to 5:1, from 0.5:1 to 2:1, from 0.8:1 to 8:1, from 0.8:1 to 4:1, or from 0.8:1 to 1.8:1, and the like.

In general, the second composition is predominantly $C_{12}$ hydrocarbons (inclusive of $C_{12}$ mono-olefins), and often the second composition contains at least 90 wt. % $C_{12}$ hydrocarbons, at least 95 wt. % $C_{12}$ hydrocarbons, at least 96 wt. % $C_{12}$ hydrocarbons, at least 97 wt. % $C_{12}$ hydrocarbons, at least 98 wt. % $C_{12}$ hydrocarbons, or at least 99 wt. % $C_{12}$ hydrocarbons.

$C_{14}$ Compositions

A third composition disclosed herein can comprise at least 60 wt. % $C_{14}$ mono-olefins. In some aspects, the third composition can comprise at least 65 wt. % $C_{14}$ mono-olefins, at least 70 wt. % $C_{14}$ mono-olefins, at least 80 wt. % $C_{14}$ mono-olefins, or at least 85 wt. % $C_{14}$ mono-olefins. Therefore, illustrative and non-limiting ranges for the amount of $C_{14}$ mono-olefins in the composition can include from 55 to 98 wt. %, from 60 to 99 wt. %, from 60 to 80 wt. %, from 68 to 96 wt. %, from 70 to 95 wt. %, from 75 to 98 wt. %, from 75 to 95 wt. %, or from 80 to 97.5 wt. %, and the like.

In the third composition, the $C_{14}$ mono-olefins can comprise at least 12 wt. % 1-tetradecene and at least 0.5 wt. % 8-nonen-1-yl-cyclopentane, and the third composition also can comprise a total of from 3 to 30 wt. % of n-tetradecane and nonylcyclopentane. While not limited thereto, the amount of 1-tetradecene, based on the total $C_{14}$ mono-olefins in the composition, often can range from 12 to 50 wt. %. In one aspect, for example, the $C_{14}$ mono-olefins can contain from 14 to 45 wt. % 1-tetradecene, while in another aspect, from 15 to 40 wt. %, and from 16 to 38 wt. % in another aspect, from 18 to 36 wt. % in yet another aspect, and from 20 to 35 wt. % in still another aspect.

At least 22 wt. % of the $C_{14}$ mono-olefins in the third composition can be non-cyclic branched $C_{14}$ mono-olefins. Representative non-cyclic branched $C_{14}$ mono-olefins can include, but are not limited to, 7-methyl-1-tridecene, 6-ethyl-1-dodecene, 5-propyl-1-undecene, 4-butyl-1-decene, 3-pentyl-1-nonene, and the like, as well as any combination thereof. In some aspects, from 25 to 85 wt. % of the $C_{14}$ mono-olefins in the third composition are non-cyclic branched $C_{14}$ mono-olefins, such as from 30 to 80 wt. %, from 45 to 80 wt. %, from 55 to 70 wt. %, from 36 to 78 wt. %, or from 50 to 75 wt. %, and the like.

At least 0.5 wt. % of the $C_{14}$ mono-olefins in the third composition can be 8-nonen-1-yl-cyclopentane. Typical ranges for the amount of 8-nonen-1-yl-cyclopentane in the $C_{14}$ mono-olefins include, but are not limited to, from 0.5 to 30 wt. %, from 0.75 to 28 wt. %, from 1.5 to 26 wt. %, from 2 to 24 wt. %, or from 5 to 15 wt. %.

In the third composition, the weight ratio of 1-tetradecene to 8-nonen-1-yl-cyclopentane typically falls within a range from 0:5:1 to 15:1. In one aspect, the ratio is in a range from 0.75:1 to 12:1, while in another aspect, the ratio is in a range from 1:1 to 10:1, and in yet another aspect, the ratio is in a range from 1.5:1 to 9:1, and in still another aspect, the ratio is in a range from 2:1 to 8:1. Additionally or alternatively, the weight ratio of non-cyclic branched $C_{14}$ mono-olefins to 8-nonen-1-yl-cyclopentane in the third composition often ranges from 0.5:1 to 50:1, from 0.75:1 to 45:1, from 15:1 to 42:1, from 30:1 to 40:1, from 0.75:1 to 30:1, from 1:1 to 15:1, or from 1.25:1 to 10:1.

In addition to $C_{14}$ mono-olefins, the third composition also can contain non-olefinic hydrocarbons, such as alkanes like n-tetradecane and nonylcyclopentane at a total amount of from 3 to 30 wt. %. While not limited thereto, the amount of n-tetradecane in the third composition can range from 0.5 to 18 wt. %, from 1 to 16 wt. %, from 2 to 12 wt. %, from 1.25 to 15 wt. %, or from 3 to 9 wt. %. The amount of nonylcyclopentane in the composition can range from 0.5 to 22 wt. %, from 1 to 20 wt. %, from 1 to 14 wt. %, from 1.25 to 18 wt. %, or from 3 to 10 wt. %, although not limited thereto. The total amount of n-tetradecane and nonylcyclopentane in the third composition can vary from 3 to 30 wt. %, and other suitable range include, but are not limited to, from 3 to 28 wt. %, from 3 to 26 wt. %, from 4 to 28 wt. %, from 5 to 25 wt. %, or from 6 to 20 wt. %, and the like.

In general, the third composition is predominantly $C_{14}$ hydrocarbons (inclusive of $C_{14}$ mono-olefins), and often the third composition contains at least 90 wt. % $C_{14}$ hydrocarbons, at least 95 wt. % $C_{14}$ hydrocarbons, at least 96 wt. % $C_{14}$ hydrocarbons, at least 97 wt. % $C_{14}$ hydrocarbons, at least 98 wt. % $C_{14}$ hydrocarbons, or at least 99 wt. % $C_{14}$ hydrocarbons.

Compositions Containing $C_{10}$ to $C_{18}$ Olefins

Another composition consistent with aspects of this invention can be referred to as a $C_{10}$-$C_{12}$ composition, and this composition generally can contain from 30 to 60 wt. % of the first composition (and any of the features of the first composition described herein) and from 38 to 68 wt. % of the second composition (and any of the features of the second composition described herein). Other amounts of the first composition in the $C_{10}$-$C_{12}$ composition can be present, thus for instance, the $C_{10}$-$C_{12}$ composition can contain from 35 to 55 wt. %, or from 40 to 50 wt. %, of the first composition. Additionally or alternatively, the $C_{10}$-$C_{12}$ composition can contain from 43 to 63 wt. %, or from 48 to 58 wt. %, of the second composition. In general, the $C_{10}$-$C_{12}$ composition is predominantly comprised of the first composition and the second composition. Accordingly, the first composition and the second composition, collectively, can represent at least 90 wt. %, at least 95 wt. %, at least 97 wt. %, at least 98 wt. %, at least 99 wt. %, or at least 99.5 wt. %, of the $C_{10}$-$C_{12}$ composition.

Illustrative and non-limiting ranges for the amount of $C_{10-12}$ mono-olefins in the $C_{10-12}$ composition can include from 60 to 99 wt. %, from 70 to 98 wt. %, from 75 to 95 wt. %, or from 80 to 95 wt. %, and the like. Similar to the first composition and the second composition, the $C_{10}$-$C_{12}$ composition also can contain, in addition to $C_{10}$-$C_{12}$ mono-olefins, non-olefinic hydrocarbons such as alkanes. In general, the $C_{10}$-$C_{12}$ composition is predominantly $C_{10}$-$C_{12}$ hydrocarbons, and often the $C_{10}$-$C_{12}$ composition contains at least 90 wt. % $C_{10}$-$C_{12}$ hydrocarbons, at least 95 wt. % $C_{10}$-$C_{12}$ hydrocarbons, at least 96 wt. % $C_{10}$-$C_{12}$ hydrocarbons, at least 97 wt. % $C_{10}$-$C_{12}$ hydrocarbons, at least 98 wt. % $C_{10}$-$C_{12}$ hydrocarbons, or at least 99 wt. % $C_{10}$-$C_{12}$ hydrocarbons.

Another composition consistent with aspects of this invention can be referred to as a $C_{12}$-$C_{14}$ composition, and this composition generally can contain from 45 to 85 wt. % of the second composition (and any of the features of the second composition described herein) and from 20 to 50 wt. % of the third composition (and any of the features of the third composition described herein). Other amounts of the second composition in the $C_{12}$-$C_{14}$ composition can be present, thus for instance, the $C_{12}$-$C_{14}$ composition can contain from 55 to 75 wt. %, or from 60 to 70 wt. %, of the second composition. Additionally or alternatively, the $C_{12}$-$C_{14}$ composition can contain from 25 to 45 wt. %, or from 30 to 40 wt. %, of the third composition. In general, the $C_{12}$-$C_{14}$ composition is predominantly comprised of the second composition and the third composition. Accordingly, the second composition and the third composition, collectively, can represent at least 90 wt. %, at least 95 wt. %, at least 97 wt. %, at least 98 wt. %, at least 99 wt. %, or at least 99.5 wt. %, of the $C_{12}$-$C_{14}$ composition.

Illustrative and non-limiting ranges for the amount of $C_{12}$-14 mono-olefins in the $C_{12}$-14 composition can include from 60 to 99 wt. %, from 70 to 98 wt. %, from 75 to 95 wt. %, or from 80 to 95 wt. %, and the like. Similar to the second composition and the third composition, the $C_{12}$-$C_{14}$ composition also can contain, in addition to $C_{12}$-$C_{14}$ mono-olefins, non-olefinic hydrocarbons such as alkanes. In general, the $C_{12}$-$C_{14}$ composition is predominantly $C_{12}$-$C_{14}$ hydrocarbons, and often the $C_{12}$-$C_{14}$ composition contains at least 90 wt. % $C_{12}$-$C_{14}$ hydrocarbons, at least 95 wt. % $C_{12}$-$C_{14}$ hydrocarbons, at least 96 wt. % $C_{12}$-$C_{14}$ hydrocarbons, at least 97 wt. % $C_{12}$-$C_{14}$ hydrocarbons, at least 98 wt. % $C_{12}$-$C_{14}$ hydrocarbons, or at least 99 wt. % $C_{12}$-$C_{14}$ hydrocarbons.

Yet another composition consistent with aspects of this invention can be referred to as a $C_{10}$-$C_{14}$ composition, and this composition generally can contain from 25 to 47 wt. % of the first composition (and any of the features of the first composition described herein), from 30 to 55 wt. % of the second composition (and any of the features of the second composition described herein), and from 12 to 35 wt. % of the third composition (and any of the features of the third composition described herein). Other amounts of the first composition in the $C_{10}$-$C_{14}$ composition can be present, thus for instance, the $C_{10}$-$C_{14}$ composition can contain from 30 to 42 wt. %, or from 33 to 39 wt. %, of the first composition. Additionally or alternatively, the $C_{10}$-$C_{14}$ composition can contain from 35 to 47 wt. %, or from 38 to 44 wt. %, of the second composition. Additionally or alternatively, the $C_{10}$-$C_{14}$ composition can contain from 15 to 27 wt. %, or from 18 to 24 wt. %, of the third composition. In general, the $C_{10}$-$C_{14}$ composition is predominantly comprised of the first composition, the second composition, and the third composition. Accordingly, the first composition, the second composition, and the third composition, collectively, can represent at least 90 wt. %, at least 95 wt. %, at least 97 wt. %, at least 98 wt. %, at least 99 wt. %, or at least 99.5 wt. %, of the $C_{10}$-$C_{14}$ composition.

Illustrative and non-limiting ranges for the amount of $C_{10\text{-}14}$ mono-olefins in the $C_{10\text{-}14}$ composition can include from 60 to 99 wt. %, from 70 to 98 wt. %, from 75 to 95 wt. %, or from 80 to 95 wt. %, and the like. Similar to the first, second, and third compositions, the $C_{10}$-$C_{14}$ composition also can contain, in addition to $C_{10}$-$C_{14}$ mono-olefins, non-olefinic hydrocarbons such as alkanes. In general, the $C_{10}$-$C_{14}$ composition is predominantly $C_{10}$-$C_{14}$ hydrocarbons, and often the $C_{10}$-$C_{14}$ composition contains at least 90 wt. % $C_{10}$-$C_{14}$ hydrocarbons, at least 95 wt. % $C_{10}$-$C_{14}$ hydrocarbons, at least 96 wt. % $C_{10}$-$C_{14}$ hydrocarbons, at least 97 wt. % $C_{10}$-$C_{14}$ hydrocarbons, at least 98 wt. % $C_{10}$-$C_{14}$ hydrocarbons, or at least 99 wt. % $C_{10}$-$C_{14}$ hydrocarbons.

Still another composition consistent with aspects of this invention can be referred to as a $C_{10}$-$C_{18}$ composition, and this composition generally can contain from 15 to 40 wt. % of the first composition (and any of the features of the first composition described herein), from 19 to 40 wt. % of the second composition (and any of the features of the second composition described herein), from 7 to 25 wt. % of the third composition (and any of the features of the third composition described herein), and from 18 to 40 wt. % of $C_{16}$-$C_{18}$ hydrocarbons. Other amounts of the first composition in the $C_{10}$-$C_{18}$ composition can be present, thus for instance, the $C_{10}$-$C_{18}$ composition can contain from 19 to 35 wt. %, or from 22 to 30 wt. %, of the first composition. Additionally or alternatively, the $C_{10}$-$C_{18}$ composition can contain from 23 to 36 wt. %, or from 27 to 33 wt. %, of the second composition. Additionally or alternatively, the $C_{10}$-$C_{18}$ composition can contain from 10 to 22 wt. %, or from 13 to 19 wt. %, of the third composition. Additionally or alternatively, the $C_{10}$-$C_{18}$ composition can contain at least 22 wt. %, at least 25 wt. %, from 22 to 36 wt. %, or from 25 to 33 wt. %, of $C_{16}$-$C_{18}$ hydrocarbons. In general, the $C_{10}$-$C_{18}$ composition is predominantly comprised of the first composition, the second composition, the third composition, and $C_{16}$-$C_{18}$ hydrocarbons.

Accordingly, the first composition, the second composition, the third composition, and $C_{16}$-$C_{18}$ hydrocarbons, collectively, can represent at least 90 wt. %, at least 95 wt. %, at least 97 wt. %, at least 98 wt. %, at least 99 wt. %, or at least 99.5 wt. %, of the $C_{10}$-$C_{18}$ composition.

Illustrative and non-limiting ranges for the amount of $C_{10\text{-}18}$ mono-olefins in the $C_{10\text{-}18}$ composition can include from 60 to 99 wt. %, from 70 to 98 wt. %, from 75 to 95 wt. %, or from 80 to 95 wt. %, and the like. Similar to the first, second, and third compositions, the $C_{10}$-$C_{18}$ composition also can contain, in addition to $C_{10}$-$C_{18}$ mono-olefins, non-olefinic hydrocarbons such as alkanes. In general, the $C_{10}$-$C_{18}$ composition is predominantly $C_{10}$-$C_{18}$ hydrocarbons, and often the $C_{10}$-$C_{18}$ composition contains at least 90 wt. % $C_{10}$-$C_{18}$ hydrocarbons, at least 95 wt. % $C_{10}$-$C_{18}$ hydrocarbons, at least 96 wt. % $C_{10}$-$C_{18}$ hydrocarbons, at least 97 wt. % $C_{10}$-$C_{18}$ hydrocarbons, at least 98 wt. % $C_{10}$-$C_{18}$ hydrocarbons, or at least 99 wt. % $C_{10}$-$C_{18}$ hydrocarbons.

EXAMPLES

The invention is further illustrated by the following examples, which are not to be construed in any way as imposing limitations to the scope of this invention. Various other aspects, modifications, and equivalents thereof which, after reading the description herein, can suggest themselves to one of ordinary skill in the art without departing from the spirit of the present invention or the scope of the appended claims.

Ethylene Oligomerization Experiment 1 was used to produce an oligomer product and followed this procedure: In a dry box, a 20-mL glass vial was charged with a pre-catalyst (5 µmol) (a $N^2$-phosphinyl guanidine chromium(III) trichloride tetrahydrofuran complex), 1 g ethylbenzene, and triethylaluminum (TEA) to achieve an Al:Cr molar ratio of 80:1.

The initial pre-catalyst slurry became a homogenous solution while stirring for 15 min. The solution was then treated with MMAO-21 (7 wt. % Al in cyclohexane, Al:Cr of 400:1) and stirred for 105 min. The activated pre-catalyst solution was then added to a 0.5-L glass charger containing a total of 200 mL of cyclohexane and 1-heptene (optionally, for analytical differentiation) and transferred into an evacuated 0.5 L stainless steel reactor heated to 70° C. Hydrogen (50 psig) was charged into the reactor followed by ethylene (875 psig). The reaction proceeded to exotherm to the target temperature of 85° C. with ethylene being fed on-demand to maintain the desired reactor pressure. After 20-30 min, the oligomerization reaction was rapidly cooled to 30° C., and then the unreacted ethylene and hydrogen gas were vented. A 2-mL sample of the liquid sample was collected, filtered, and analyzed by GC-FID. The three runs (one with heptene and two without) of Experiment 1 produced nominal solids.

GC-FID data was collected on an Agilent Technologies 7890A instrument equipped with a 50 m length Agilent DB-5 GC column with an inner diameter of 0.32 mm and film thickness of 0.25 μm. The sample (0.05 μL) was syringe injected into the inlet with a split ratio of 25:1 at 300° C. using Ile as the carrier gas. The initial column temperature was 40° C. with a temperature ramp rate of 3° C./min up to 80° C., followed by a 13° C./min ramp up to 300° C. and a 15 min hold time. Peak integration was performed manually and peak identification was made using authentic samples.

Table 1 summarizes the oligomer distribution of the products formed from Ethylene Oligomerization Experiment 1 (with no heptene). The bulk of the heavy (>$C_8$) oligomers formed fell in the $C_{10}$ to $C_{14}$ range. The total amount of $C_{10}$-$C_{14}$ products (7.65 g) was over twice that of the remaining heavier oligomers (3.06 g). Primary $C_6$ and $C_8$ products (total of 105.26 g) were the vast majority of the oligomer product. $C_{10}$ and $C_{12}$ fractions were produced in similar amounts, while the $C_{14}$ fraction was about half that of either $C_{10}$ or $C_{12}$.

The measured distribution in Table 2 summarizes the breakdown (in wt. %) of the $C_{10}$ fraction produced in Ethylene Oligomerization Experiment 1. The skewed cyclic and skewed linear columns are prophetic distributions if cyclic mechanisms and linear mechanisms, respectively, were favored. While not wishing to be bound by the following theory, it is believed that cyclic mechanisms are enhanced with higher ethylene conversions, higher 1-hexene/1-octene product ratios, higher oligomerization temperatures, and lower chromium contents in the reaction zone. Conversely, it is believed that lower oligomerization temperatures and higher hydrogen contents in the reaction zone enhance linear mechanisms.

Table 3 summarizes four possible mechanisms that can possibly produce up to sixteen $C_{10}$ species from ethylene and 1-hexene or 1-octene. Unexpectedly, 3-methylnonane is unique to the linear dimerization mechanism, while 5-methylnonane is unique to the linear trimerization mechanism. While 4-penten-1-yl-cyclopentane and pentylcyclopentane also are unique to the linear trimerization mechanism as noted in Table 3, it is believed that these species also may be formed by ethylene insertion into a chromium catalyst intermediate.

Several species from the measured distribution in Table 2 are reproduced in the inventive column of Table 4. The comparative column represents results from Ethylene Oligomerization Experiment 2, an oligomerization experiment performed as described above, except that the chromium pre-catalyst was (PNP)CrCl$_3$(THF) (PNP is Ph$_2$PN(iPr)PPh$_2$, where Ph is phenyl and iPr is isopropyl), the oligomerization temperature was 70° C., and no TEA was used. A lower temperature was used for the comparative example to reduce the amount of polymer that was produced at higher temperatures. Unexpectedly, the inventive example (Ethylene Oligomerization Experiment 1) had significantly less 1-decene and significantly more 4-penten-1-yl-cyclopentane and pentylcyclopentane. Interestingly, since higher oligomerization temperatures favor cyclic mechanisms, if the comparative example (Ethylene Oligomerization Experiment 2) was suitable for testing at the same (higher) temperature as the inventive example, it is believed that even less 4-penten-1-yl-cyclopentane and pentylcyclopentane would have been produced in the comparative example (based on the information in Tables 2-3.

Referring now to the $C_{12}$ products, the measured distribution in Table 5 summarizes the breakdown (in wt. %) of the $C_{12}$ fraction produced in Ethylene Oligomerization Experiment 1. The skewed cyclic and skewed linear columns are prophetic distributions if cyclic mechanisms and linear mechanisms, respectively, were favored. Again, while not wishing to be bound by the following theory, it is believed that cyclic mechanisms are enhanced with higher ethylene conversions, higher 1-hexene/1-octene product ratios, higher oligomerization temperatures, and lower chromium contents in the reaction zone. Conversely, it is believed that lower oligomerization temperatures and higher hydrogen contents in the reaction zone enhance linear mechanisms. The 1-dodecene, n-dodecane, heptylcyclopentane, and 6-hepten-1-ylcyclopentane species were conclusively identified and quantified by GC-MS (same GC method as above, but a different analyzer). However, the other compounds in Table 5 (e.g., non-cyclic branched $C_{12}$ mono-olefins and non-cyclic branched $C_{12}$ alkanes) were lumped into related groups and their total wt. % was estimated using GC-FID and comparative analysis, but the individual compounds were not independently verified.

Table 6 summarizes five possible mechanisms that can possibly produce up to 21 $C_{12}$ species from ethylene and 1-hexene or 1-octene. It is believed that a majority of the $C_{12}$ fraction (the non-cyclic branched $C_{12}$ mono-olefins) were generated by the two metallacyclic pathways. Surprisingly, the metallacyclic trimerization pathway produced four unique alkenes (6-dodecene, 5-methyl-1-undecene, 4-ethyl-1-decene, 3-propyl-1-nonene) as well as the metallacyclic tetramerization (4-dodecene, 7-methyl-1-undecene, 6-ethyl-1-decene, 5-propyl-1-nonene). Further, unlike the $C_{10}$ fraction and $C_{14}$ fraction described herein, the $C_{12}$ fraction surprisingly appears to be predominantly generated through 1-alkene/ethylene metallacyclization.

Several species from the measured distribution in Table 5 are reproduced in the inventive column of Table 7. The comparative column represents results from Ethylene Oligomerization Experiment 2. Unexpectedly, the inventive example (Ethylene Oligomerization Experiment 1) had significantly more 6-hepten-1-ylcyclopentane and heptylcyclopentane. Interestingly, since higher oligomerization temperatures favor cyclic mechanisms, if the comparative example (Ethylene Oligomerization Experiment 2) was suitable for testing at the same (higher) temperature as the inventive example, it is believed that even less 6-hepten-1-ylcyclopentane and heptylcyclopentane would have been produced in the comparative example (based on the information in Tables 5-6.

Referring now to the $C_{14}$ products, the measured distribution in Table 8 summarizes the breakdown (in wt. %) of the $C_{14}$ fraction produced in Ethylene Oligomerization Experiment 1. The skewed cyclic and skewed linear columns are prophetic distributions if cyclic mechanisms and linear mechanisms, respectively, were favored. The 1-tetradecene, n-tetradecane, nonylcyclopentane, and 8-nonen-1-ylcyclopentane species were conclusively identified by GC-MS. However, the other compounds in Table 8 (e.g., non-cyclic branched $C_{14}$ mono-olefins and non-cyclic branched $C_{14}$ alkanes) were lumped into related groups and their total wt. % was estimated using GC-FID and comparative analysis, but the individual compounds were not independently verified.

Table 9 summarizes four possible mechanisms that can possibly produce up to fourteen $C_{14}$ species from ethylene and 1-hexene or 1-octene. It is believed that a majority of the $C_{14}$ fraction (the non-cyclic branched $C_{14}$ mono-olefins) was generated from metallacyclic tetramerization. The nonylcyclopentane and 8-nonen-1-ylcyclopentane species appear to be formed exclusively from a linear mechanism.

Several species from the measured distribution in Table 8 are reproduced in the inventive column of Table 10. The comparative column represents results from Ethylene Oligomerization Experiment 2. Unexpectedly, the inventive example (Ethylene Oligomerization Experiment 1) had significantly more n-tetradecane, 8-nonen-1-ylcyclopentane, and nonylcyclopentane. Interestingly, since higher oligomerization temperatures favor cyclic mechanisms, if the comparative example (Ethylene Oligomerization Experiment 2) was suitable for testing at the same (higher) temperature as the inventive example, it is believed that even less n-tetradecane, 8-nonen-1-ylcyclopentane, and nonylcyclopentane would have been produced in the comparative example (based on the information in Tables 8-9.

TABLE 1

| $C_6$ (g) | $C_8$ (g) | $C_{10}$ (g) | $C_{12}$ (g) | $C_{14}$ (g) | $C_{16+}$ (g) | Ethylene Conversion (mol %) |
|---|---|---|---|---|---|---|
| 46.35 | 58.91 | 2.79 | 3.19 | 1.67 | 3.06 | 4.2 |
| Total $C_6$-$C_8$ | | Total $C_{10}$-$C_{14}$ | | | | |
| 105.26 g | | 7.65 g | | | | |

TABLE 2

| Alkene/Alkane | Measured Distribution | Skewed Cyclic | Skewed Linear |
|---|---|---|---|
| 1-decene | 19 | 16 | 21 |
| 3-decene | 1 | 0 | 1 |
| 4-decene | 3 | 6 | 3 |
| 5-decene | | | |
| n-decane | 7 | 2 | 13 |
| 3-methyl-1-nonene | 4 | 0 | 5 |
| 5-methyl-1-nonene | 15 | 30 | 4 |
| 3-methylnonane | 1 | 0 | 2 |
| 5-methylnonane | 1 | 0 | 2 |
| 2-ethyl-1-octene | 3 | 1 | 3 |
| 4-ethyl-1-octene | 1 | 4 | 1 |
| 4-ethyloctane | 8 | 2 | 10 |
| 3-propyl-1-heptene | 9 | 20 | 3 |
| 2-butyl-1-hexene | 3 | 7 | 1 |
| 4-penten-1-yl-cyclopentane | 14 | 7 | 18 |
| pentylcyclopentane | 11 | 5 | 13 |

TABLE 3

| | Alkene/Alkane | Linear Dimer | Cyclic Trimer | Linear Trimer | Linear Pentamer |
|---|---|---|---|---|---|
| 1 | 1-decene | X | X | X | X |
| 2 | 3-decene | X | | | |
| 3 | 4-decene | X | X | X | |
| 4 | 5-decene | | X | X | |
| 5 | n-decane | X | | X | X |
| 6 | 3-methyl-1-nonene | X | | | |
| 7 | 5-methyl-1-nonene | | X | X | |
| 8 | 3-methylnonane | X | | | |
| 9 | 5-methylnonane | | | X | |
| 10 | 2-ethyl-1-octene | X | | | |
| 11 | 4-ethyl-1-octene | | X | X | |
| 12 | 4-ethyloctane | | | X | |
| 13 | 3-propyl-1-heptene | | X | X | |
| 14 | 2-butyl-1-hexene | | X | X | |
| 15 | 4-penten-1-yl-cyclopentane | | | X | |
| 16 | pentylcyclopentane | | | X | |

TABLE 4

| Alkene/Alkane | Inventive | Comparative |
|---|---|---|
| 1-decene | 19 | 48 |
| n-decane | 7 | 2 |
| 4-penten-1-yl-cyclopentane | 14 | 5 |
| pentylcyclopentane | 11 | 3 |

TABLE 5

| Alkene/Alkane | Measured Distribution | Skewed Cyclic | Skewed Linear |
|---|---|---|---|
| 1-dodecene | 14 | 12 | 18 |
| 4-dodecene | 1 | 1 | 2 |
| 5-dodecene | | | |
| 6-dodecene | | | |
| n-dodecane | 4 | 1 | 12 |
| 5-methyl-1-undecene | 65 | 82 | 22 |
| 7-methyl-1-undecene | | | |
| 4-ethyl-1-decene | | | |
| 6-ethyl-1-decene | | | |
| 3-propyl-1-nonene | | | |
| 5-propyl-1-nonene | | | |
| 2-butyl-1-octene | | | |
| 3-butyl-1-octene | | | |
| 4-butyl-1-octene | | | |
| 5-methylundecane | 3 | 1 | 8 |
| 4-ethyldecane | | | |
| 5-ethyldecane | | | |
| 3-propylnonane | | | |
| 5-propylnonane | | | |
| 6-hepten-1-ylcyclopentane | 7 | 2 | 20 |
| heptylcyclopentane | 6 | 1 | 18 |

TABLE 6

| | Alkene/Alkane | Cyclic Trimer | Linear Trimer | Cyclic Tetramer | Linear Tetramer | Linear Hexamer |
|---|---|---|---|---|---|---|
| 1 | 1-dodecene | X | X | X | X | X |
| 2 | 4-dodecene | | | X | X | |
| 3 | 5-dodecene | X | X | X | X | |
| 4 | 6-dodecene | X | X | | | |
| 5 | n-dodecane | | X | | X | X |
| 6 | 5-methyl-1-undecene | X | X | | | |
| 7 | 7-methyl-1-undecene | | | X | X | |
| 8 | 5-methylundecane | | X | | X | |
| 9 | 4-ethyl-1-decene | X | X | | | |
| 10 | 6-ethyl-1-decene | | | X | X | |
| 11 | 4-ethyldecane | | X | | X | |
| 12 | 5-ethyldecane | | X | | X | |
| 13 | 3-propyl-1-nonene | X | X | | | |
| 14 | 5-propyl-1-nonene | | | X | X | |
| 15 | 3-propylnonane | | X | | X | |
| 16 | 5-propylnonane | | X | | X | |
| 17 | 2-butyl-1-octene | X | X | X | X | |
| 18 | 3-butyl-1-octene | | | X | X | |
| 19 | 4-butyl-1-octene | | | X | X | |
| 20 | 6-hepten-1-ylcyclopentane | | | | X | |
| 21 | heptylcyclopentane | | | | X | |

TABLE 7

| Alkene/Alkane | Inventive | Comparative |
|---|---|---|
| 1-dodecene | 14 | 12 |
| n-dodecane | 4 | 10 |
| 6-hepten-1-ylcyclopentane | 7 | 1 |
| heptylcyclopentane | 6 | 1 |

TABLE 8

| Alkene/Alkane | Measured Distribution | Skewed Cyclic | Skewed Linear |
|---|---|---|---|
| 1-tetradecene | 21 | 18 | 24 |
| 6-tetradecene | 2 | 1 | 3 |
| 7-tetradecene | | | |
| n-tetradecane | 6 | 2 | 12 |
| 7-methyl-1-tridecene | 53 | 75 | 25 |
| 6-ethyl-1-dodecene | | | |
| 5-propyl-1-undecene | | | |
| 4-butyl-1-decene | | | |
| 3-pentyl-1-nonene | | | |
| 7-methyltridecane | 3 | 1 | 6 |
| 6-ethyldodecane | | | |
| 5-propyl-1-undecane | | | |
| 8-nonen-1-ylcyclopentane | 8 | 2 | 16 |
| nonylcyclopentane | 7 | 1 | 14 |

TABLE 9

| | Alkene/Alkane | Cyclic Tetramer | Linear Tetramer | Linear Pentamer | Linear Heptamer |
|---|---|---|---|---|---|
| 1 | 1-tetradecene | X | X | | X |
| 2 | 6-tetradecene | X | X | | |
| 3 | 7-tetradecene | X | X | | |
| 4 | n-tetradecane | | X | | X |
| 5 | 7-methyl-1-tridecene | X | X | | |
| 6 | 7-methyltridecane | | X | | |
| 7 | 6-ethyl-1-dodecene | X | X | | |
| 8 | 6-ethyldodecane | | X | | |
| 9 | 5-propyl-1-undecene | X | X | | |
| 10 | 5-propyl-1-undecane | | X | | |
| 11 | 4-butyl-1-decene | X | X | | |
| 12 | 3-pentyl-1-nonene | X | X | | |
| 13 | 8-nonen-1-ylcyclopentane | | | X | |
| 14 | nonylcyclopentane | | | X | |

TABLE 10

| Alkene/Alkane | Inventive | Comparative |
|---|---|---|
| 1-tetradecene | 21 | 13 |
| n-tetradecane | 6 | 1 |
| 8-nonen-1-ylcyclopentane | 8 | 1 |
| nonylcyclopentane | 7 | 1 |

The invention is described herein with reference to numerous aspects and specific examples. Many variations will suggest themselves to those skilled in the art in light of the detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A composition comprising at least 55 wt. % $C_{10}$ mono-olefins, the $C_{10}$ mono-olefins comprising:
  i) from 11 to 45 wt. % 1-decene;
  ii) at least 0.5 wt. % 2-butyl-1-hexene;
  iii) at least 1 wt. % 3-propyl-1-heptene;
  iv) from 0.5 to 12 wt. % wt. % 4-ethyl-1-octene;
  v) at least 4 wt. % 4-penten-1-yl-cyclopentane; and
  vi) from 2 to 40 wt. % 5-methyl-1-nonene.

Aspect 2. The composition defined in aspect 1, wherein the $C_{10}$ mono-olefins comprise any suitable amount of 1-decene or any amount disclosed herein, e.g., from 12 to 42 wt. %, from 12 to 30 wt. %, from 15 to 38 wt. %, from 17 to 35 wt. %, or from 20 to 30 wt. %.

Aspect 3. The composition defined in aspect 1 or 2, wherein the $C_{10}$ mono-olefins comprise any suitable amount of 2-butyl-1-hexene or any amount disclosed herein, e.g., from 0.5 to 12 wt. %, from 0.75 to 12 wt. %, from 1 to 8 wt. %, or from 2 to 6 wt. %.

Aspect 4. The composition defined in any one of the preceding aspects, wherein the $C_{10}$ mono-olefins comprise any suitable amount of 3-propyl-1-heptene or any amount disclosed herein, e.g., from 1 to 27 wt. %, from 3 to 25 wt. %, from 5 to 22 wt. %, or from 7 to 17 wt. %.

Aspect 5. The composition defined in any one of the preceding aspects, wherein the $C_{10}$ mono-olefins comprise any suitable amount of 4-ethyl-1-octene or any amount disclosed herein, e.g., from 0.5 to 10 wt. %, from 0.75 to 7 wt. %, from 0.75 to 5 wt. %, from 1 to 5 wt. %, or from 1 to 4 wt. %.

Aspect 6. The composition defined in any one of the preceding aspects, wherein the $C_{10}$ mono-olefins comprise any suitable amount of 4-penten-1-yl-cyclopentane or any amount disclosed herein, e.g., from 4 to 40 wt. %, from 4 to 37 wt. %, from 5 to 34 wt. %, from 7 to 30 wt. %, or from 10 to 25 wt. %.

Aspect 7. The composition defined in any one of the preceding aspects, wherein the $C_{10}$ mono-olefins comprise any suitable amount of 5-methyl-1-nonene or any amount disclosed herein, e.g., from 2 to 38 wt. %, from 4 to 40 wt. %, from 4 to 33 wt. %, from 6 to 33 wt. %, or from 10 to 28 wt. %.

Aspect 8. The composition defined in any one of the preceding aspects, wherein the $C_{10}$ mono-olefins further comprise any suitable amount of 2-ethyl-1-octene or any amount disclosed herein, e.g., from 0.3 to 8 wt. %, from 0.5 to 5 wt. %, from 1 to 5 wt. %, or from 0.8 to 4 wt. %.

Aspect 9. The composition defined in any one of the preceding aspects, wherein the $C_{10}$ mono-olefins further comprise any suitable amount of 3-methyl-1-nonene or any amount disclosed herein, e.g., from greater than 0 to 10 wt. %, from greater than 0 to 8 wt. %, from greater than 0 to 6 wt. %, or from 2 to 7 wt. %.

Aspect 10. The composition defined in any one of the preceding aspects, wherein the composition further comprises any suitable amount of pentylcyclopentane or any amount disclosed herein, e.g., from 1 to 20 wt. %, from 2 to 18 wt. %, from 3 to 15 wt. %, from 5 to 13 wt. %, or from 7 to 13 wt. %.

Aspect 11. The composition defined in any one of the preceding aspects, wherein the $C_{10}$ mono-olefins comprise any suitable weight ratio of (2-butyl-1-hexene+3-propyl-1-heptene+4-ethyl-1-octene+5-methyl-1-nonene) to 1-decene or any weight ratio disclosed herein, e.g., from 0.2:1 to 10:1, from 0.3:1 to 8:1, from 0.35:1 to 6:1, from 0.4:1 to 5:1, or from 0.8:1 to 5:1.

Aspect 12. The composition defined in any one of the preceding aspects, wherein the $C_{10}$ mono-olefins comprise any suitable weight ratio of 4-penten-1-yl-cyclopentane to 1-decene or any weight ratio disclosed herein, e.g., from 0:1:1 to 3:1, from 0.2:1 to 2:1, from 0.2:1 to 1.2:1, from 0.3:1 to 1.5:1, from 0.3:1 to 1:1, or from 0.4:1 to 0.9:1.

Aspect 13. The composition defined in any one of the preceding aspects, wherein the $C_{10}$ mono-olefins comprise any suitable weight ratio of (2-butyl-1-hexene+3-propyl-1-heptene+4-ethyl-1-octene+5-methyl-1-nonene) to 4-penten-1-yl-cyclopentane or any weight ratio disclosed herein, e.g., from 0.1:1 to 12:1, from 0.4:1 to 10:1, from 4:1 to 10:1, from 6:1 to 9:1, from 0.3:1 to 4:1, or from 0.4:1 to 3:1.

Aspect 14. The composition defined in any one of the preceding aspects, wherein the composition comprises any suitable amount of $C_{10}$ mono-olefins or any amount disclosed herein, e.g., from 55 to 98 wt. %, from 70 to 95 wt. %, from 85 to 95 wt. %, from 55 to 85 wt. %, from 60 to 92 wt. %, or from 65 to 85 wt. %.

Aspect 15. The composition defined in any one of the preceding aspects, wherein the composition comprises any suitable amount of $C_{10}$ hydrocarbons or any amount disclosed herein, e.g., at least 90 wt. %, at least 95 wt. %, at least 96 wt. %, at least 97 wt. %, or at least 98 wt. %.

Aspect 16. A composition comprising at least 60 wt. % $C_{12}$ mono-olefins, the $C_{12}$ mono-olefins comprising i) at least 8 wt. % 1-dodecene and ii) at least 0.5 wt. % 6-hepten-1-yl-cyclopentane; wherein the composition comprises heptylcyclopentane and n-dodecane at a weight ratio of heptylcyclopentane to n-dodecane from 0:3:1 to 8:1.

Aspect 17. The composition defined in aspect 16, wherein the $C_{12}$ mono-olefins comprise any suitable amount of 1-dodecene or any amount disclosed herein, e.g., from 8 to 40 wt. %, from 9 to 35 wt. %, from 10 to 33 wt. %, from 12 to 29 wt. %, or from 13 to 23 wt. %.

Aspect 18. The composition defined in aspect 16 or 17, wherein the $C_{12}$ mono-olefins further comprise any suitable amount of non-cyclic branched $C_{12}$ mono-olefins or any amount disclosed herein, e.g., from 22 to 90 wt. %, from 29 to 88 wt. %, from 60 to 86 wt. %, from 60 to 80 wt. %, from 35 to 85 wt. %, from 33 to 50 wt. %, or from 33 to 40 wt. %.

Aspect 19. The composition defined in any one of aspects 16-18, wherein the non-cyclic branched $C_{12}$ mono-olefins comprise 5-methyl-1-undecene, 7-methyl-1-undecene, 4-ethyl-1-decene, 6-ethyl-1-decene, 3-propyl-1-nonene, 5-propyl-1-nonene, 2-butyl-1-octene, 3-butyl-1-octene, 4-butyl-1-octene, or any combination thereof.

Aspect 20. The composition defined in any one of aspects 16-19, wherein the $C_{12}$ mono-olefins comprise any suitable amount of 6-hepten-1-yl-cyclopentane or any amount disclosed herein, e.g., from 0.5 to 40 wt. %, from 1 to 35 wt. %, from 2 to 40 wt. %, from 2 to 32 wt. %, from 3 to 20 wt. %, or from 4 to 15 wt. %.

Aspect 21. The composition defined in any one of aspects 16-20, wherein the composition comprises any suitable amount of heptylcyclopentane or any amount disclosed herein, e.g., from 0.25 to 25 wt. %, from 0.5 to 23 wt. %, from 1 to 23 wt. %, from 3 to 20 wt. %, from 1 to 18 wt. %, or from 3 to 10 wt. %.

Aspect 22. The composition defined in any one of aspects 16-21, wherein the composition comprises any suitable amount of n-dodecane or any amount disclosed herein, e.g., from 0.25 to 18 wt. %, from 0.5 to 16 wt. %, from 0.5 to 10 wt. %, from 0.75 to 8 wt. %, from 1 to 12 wt. %, from 8 to 14 wt. %, or from 0.75 to 10 wt. %.

Aspect 23. The composition defined in any one of aspects 16-22, wherein the $C_{12}$ mono-olefins comprise any suitable weight ratio of 1-dodecene to 6-hepten-1-yl-cyclopentane or any weight ratio disclosed herein, e.g., from 0:4:1 to 12:1, from 0.6 to 10:1, from 0.9:1 to 6:1, or from 1.5:1 to 4:1.

Aspect 24. The composition defined in any one of aspects 16-23, wherein the composition comprises any suitable weight ratio of heptylcyclopentane to n-dodecane or any weight ratio disclosed herein, e.g., from 0:3:1 to 6:1, from 0.3:1 to 3:1, from 0.5:1 to 5:1, from 0.5:1 to 2:1, from 0.8:1 to 8:1, from 0.8:1 to 4:1, or from 0.8:1 to 1.8:1.

Aspect 25. The composition defined in any one of aspects 16-24, wherein the composition comprises any suitable amount of $C_{12}$ mono-olefins or any amount disclosed herein, e.g., from 60 to 99 wt. %, from 62 to 97 wt. %, from 70 to 98 wt. %, or from 75 to 95 wt. %.

Aspect 26. The composition defined in any one of aspects 16-25, wherein the composition comprises any suitable amount of $C_{12}$ hydrocarbons or any amount disclosed herein, e.g., at least 90 wt. %, at least 95 wt. %, at least 96 wt. %, at least 97 wt. %, or at least 98 wt. %.

Aspect 27. A composition comprising at least 60 wt. % $C_{14}$ mono-olefins, the $C_{14}$ mono-olefins comprising i) at least 12 wt. % 1-tetradecene and ii) at least 0.5 wt. % 8-nonen-1-yl-cyclopentane; wherein the composition comprises a total of from 3 to 30 wt. % of n-tetradecane and nonylcyclopentane.

Aspect 28. The composition defined in aspect 27, wherein the $C_{14}$ mono-olefins comprise any suitable amount of 1-tetradecene or any amount disclosed herein, e.g., from 12 to 50 wt. %, from 14 to 45 wt. %, from 15 to 40 wt. %, from 16 to 38 wt. %, from 18 to 36 wt. %, or from 20 to 35 wt. %.

Aspect 29. The composition defined in aspect 27 or 28, wherein the $C_{14}$ mono-olefins further comprise any suitable amount of non-cyclic branched $C_{14}$ mono-olefins or any amount disclosed herein, e.g., from 25 to 85 wt. %, from 30 to 80 wt. %, from 45 to 80 wt. %, from 55 to 70 wt. %, from 36 to 78 wt. %, or from 50 to 75 wt. %.

Aspect 30. The composition defined in any one of aspects 27-29, wherein the non-cyclic branched $C_{14}$ mono-olefins comprise 7-methyl-1-tridecene, 6-ethyl-1-dodecene, 5-propyl-1-undecene, 4-butyl-1-decene, 3-pentyl-1-nonene, or any combination thereof.

Aspect 31. The composition defined in any one of aspects 27-30, wherein the $C_{14}$ mono-olefins comprise any suitable amount of 8-nonen-1-yl-cyclopentane or any amount disclosed herein, e.g., from 0.5 to 30 wt. %, from 0.75 to 28 wt. %, from 1.5 to 26 wt. %, from 2 to 24 wt. %, or from 5 to 15 wt. %.

Aspect 32. The composition defined in any one of aspects 27-31, wherein the composition comprises any suitable amount of nonylcyclopentane or any amount disclosed herein, e.g., from 0.5 to 22 wt. %, from 1 to 20 wt. %, from 1 to 14 wt. %, from 1.25 to 18 wt. %, or from 3 to 10 wt. %.

Aspect 33. The composition defined in any one of aspects 27-32, wherein the composition comprises any suitable amount of n-tetradecane or any amount disclosed herein, e.g., from 0.5 to 18 wt. %, from 1 to 16 wt. %, from 2 to 12 wt. %, from 1.25 to 15 wt. %, or from 3 to 9 wt. %.

Aspect 34. The composition defined in any one of aspects 27-33, wherein the $C_{14}$ mono-olefins comprise any suitable weight ratio of 1-tetradecene to 8-nonen-1-yl-cyclopentane or any weight ratio disclosed herein, e.g., from 0:5:1 to 15:1, from 0.75:1 to 12:1, from 1:1 to 10:1, from 1.5:1 to 9:1, or from 2:1 to 8:1.

Aspect 35. The composition defined in any one of aspects 27-34, wherein the composition comprises any suitable total amount of n-tetradecane and nonylcyclopentane or any amount disclosed herein, e.g., from 3 to 28 wt. %, from 3 to 26 wt. %, from 4 to 28 wt. %, from 5 to 25 wt. %, or from 6 to 20 wt. %.

Aspect 36. The composition defined in any one of aspects 27-35, wherein the composition comprises any suitable amount of $C_{14}$ mono-olefins or any amount disclosed herein, e.g., from 60 to 99 wt. %, from 68 to 96 wt. %, from 75 to 98 wt. %, or from 75 to 95 wt. %.

Aspect 37. The composition defined in any one of aspects 27-36, wherein the composition comprises any suitable amount of $C_{14}$ hydrocarbons or any amount disclosed herein, e.g., at least 90 wt. %, at least 95 wt. %, at least 96 wt. %, at least 97 wt. %, or at least 98 wt. %.

Aspect 38. A composition comprising: i) any suitable amount of the composition defined in any one of aspects 1-15 disclosed herein, e.g., from 25 to 47 wt. %, from 30 to 42 wt. %, or from 33 to 39 wt. %; ii) any suitable amount of the composition defined in any one of aspects 16-26 disclosed herein, e.g., from 30 to 55 wt. %, from 35 to 47 wt. %, or from 38 to 44 wt. %; and iii) any suitable amount of the composition defined in any one of aspects 27-37 disclosed herein, e.g., from 12 to 35 wt. %, from 15 to 27 wt. %, from 18 to 24 wt. %.

Aspect 39. The composition defined in aspect 38, wherein the composition comprises any suitable amount of $C_{10-14}$ mono-olefins or any amount disclosed herein, e.g., from 60 to 99 wt. %, from 70 to 98 wt. %, from 75 to 95 wt. %, or from 80 to 95 wt. %.

Aspect 40. The composition defined in aspect 38 or 39, wherein the composition comprises any suitable amount of $C_{10-14}$ hydrocarbons or any amount disclosed herein, e.g., at least 90 wt. %, at least 95 wt. %, at least 96 wt. %, at least 97 wt. %, or at least 98 wt. %.

Aspect 41. The composition defined in any one of aspects 38-40, wherein the total amount of the composition defined in any one of aspects 1-15, the composition defined in any one of aspects 16-26, and the composition defined in any one of aspects 27-37 is any amount disclosed herein, e.g., at least 95 wt. %, at least 97 wt. %, at least 98 wt. %, at least 99 wt. %, or at least 99.5 wt. %.

Aspect 42. A composition comprising: i) any suitable amount of the composition defined in any one of aspects 1-15 disclosed herein, e.g., from 15 to 40 wt. %, from 19 to 35 wt. %, or from 22 to 30 wt. %, ii) any suitable amount of the composition defined in any one of aspects 16-26 disclosed herein, e.g., from 19 to 40 wt. %, from 23 to 36 wt. %, or from 27 to 33 wt. %; iii) any suitable amount of the composition defined in any one of aspects 27-37 disclosed herein, e.g., from 7 to 25 wt. %, from 10 to 22 wt. %, or from 13 to 19 wt. %; and iv) any suitable total amount of $C_{16}$ hydrocarbons and $C_{18}$ hydrocarbons disclosed herein, e.g., at least 18 wt. %, at least 22 wt. %, at least 25 wt. %, from 18 to 40 wt. %, from 22 to 36 wt. %, or from 25 to 33 wt. %.

Aspect 43. The composition defined in aspect 42, wherein the composition comprises any suitable amount of $C_{10-18}$ mono-olefins or any amount disclosed herein, e.g., from 60 to 99 wt. %, from 70 to 98 wt. %, from 75 to 95 wt. %, or from 80 to 95 wt. %.

Aspect 44. The composition defined in aspect 42 or 43, wherein the composition comprises any suitable amount of $C_{10-18}$ hydrocarbons or any amount disclosed herein, e.g., at least 90 wt. %, at least 95 wt. %, at least 96 wt. %, at least 97 wt. %, or at least 98 wt. %.

Aspect 45. The composition defined in any one of aspects 42-44, wherein the total amount of the composition defined in any one of aspects 1-15, the composition defined in any one of aspects 16-26, the composition defined in any one of aspects 27-37, $C_{16}$ hydrocarbons, and $C_{18}$ hydrocarbons is any amount disclosed herein, e.g., at least 95 wt. %, at least 97 wt. %, at least 98 wt. %, at least 99 wt. %, or at least 99.5 wt. %.

Aspect 46. A composition comprising: i) any suitable amount of the composition defined in any one of aspects 1-15 disclosed herein, e.g., from 30 to 60 wt. %, from 35 to 55 wt. %, or from 40 to 50 wt. %; and ii) any suitable amount of the composition defined in any one of aspects 16-26 disclosed herein, e.g., from 38 to 68 wt. %, from 43 to 63 wt. %, or from 48 to 58 wt. %.

Aspect 47. The composition defined in aspect 46, wherein the composition comprises any suitable amount of $C_{10-12}$ mono-olefins or any amount disclosed herein, e.g., from 60 to 99 wt. %, from 70 to 98 wt. %, from 75 to 95 wt. %, or from 80 to 95 wt. %.

Aspect 48. The composition defined in aspect 46 or 47, wherein the composition comprises any suitable amount of $C_{10-12}$ hydrocarbons or any amount disclosed herein, e.g., at least 90 wt. %, at least 95 wt. %, at least 96 wt. %, at least 97 wt. %, or at least 98 wt. %.

Aspect 49. The composition defined in any one of aspects 46-48, wherein the total amount of the composition defined in any one of aspects 1-15, and the composition defined in any one of aspects 16-26 is any amount disclosed herein, e.g., at least 95 wt. %, at least 97 wt. %, at least 98 wt. %, at least 99 wt. %, or at least 99.5 wt. %.

Aspect 50. A composition comprising: i) any suitable amount of the composition defined in any one of aspects 16-26 disclosed herein, e.g., from 45 to 85 wt. %, from 55 to 75 wt. %, or from 60 to 70 wt. %; and iii) any suitable amount of the composition defined in any one of aspects 27-37 disclosed herein, e.g., from 20 to 50 wt. %, from 25 to 45 wt. %, or from 30 to 40 wt. %.

Aspect 51. The composition defined in aspect 50, wherein the composition comprises any suitable amount of $C_{12}$-14 mono-olefins or any amount disclosed herein, e.g., from 60 to 99 wt. %, from 70 to 98 wt. %, from 75 to 95 wt. %, or from 80 to 95 wt. %.

Aspect 52. The composition defined in aspect 50 or 51, wherein the composition comprises any suitable amount of $C_{12}$-14 hydrocarbons or any amount disclosed herein, e.g., at least 90 wt. %, at least 95 wt. %, at least 96 wt. %, at least 97 wt. %, or at least 98 wt. %.

Aspect 53. The composition defined in any one of aspects 50-52, wherein the total amount of the composition defined in any one of aspects 16-26 and the composition defined in any one of aspects 27-37 is any amount disclosed herein, e.g., at least 95 wt. %, at least 97 wt. %, at least 98 wt. %, at least 99 wt. %, or at least 99.5 wt. %.

What is claimed is:

1. A composition comprising at least 55 wt. % $C_{10}$ mono-olefins, the $C_{10}$ mono-olefins comprising:
   i) from 11 to 45 wt. % 1-decene;
   ii) at least 0.5 wt. % 2-butyl-1-hexene;
   iii) at least 1 wt. % 3-propyl-1-heptene;
   iv) from 0.5 to 12 wt. % wt. % 4-ethyl-1-octene;
   v) at least 4 wt. % 4-penten-1-yl-cyclopentane; and
   vi) from 2 to 40 wt. % 5-methyl-1-nonene.

2. The composition of claim 1, wherein the $C_{10}$ mono-olefins comprise from 17 to 35 wt. % 1-decene.

3. The composition of claim 1, wherein the $C_{10}$ mono-olefins comprise from 0.75 to 7 wt. % 4-ethyl-1-octene.

4. The composition of claim 1, wherein the $C_{10}$ mono-olefins comprise a weight ratio of 4-penten-1-yl-cyclopentane to 1-decene from 0.3:1 to 1.5:1.

5. The composition of claim 1, wherein the composition comprises:
   from 60 to 92 wt. % $C_{10}$ mono-olefins; and
   from 3 to 15 wt. % pentylcyclopentane.

6. The composition of claim 5, wherein the $C_{10}$ mono-olefins comprise:
   from 1 to 8 wt. % 2-butyl-1-hexene;
   from 3 to 25 wt. % 3-propyl-1-heptene;
   from 7 to 30 wt. % 4-penten-1-yl-cyclopentane; and
   from 6 to 33 wt. % 5-methyl-1-nonene.

7. A composition comprising at least 60 wt. % $C_{12}$ mono-olefins, the $C_{12}$ mono-olefins comprising:
   i) at least 8 wt. % 1-dodecene; and
   ii) at least 0.5 wt. % 6-hepten-1-yl-cyclopentane;
   wherein the composition further comprises heptylcyclopentane and n-dodecane at a weight ratio of heptylcyclopentane to n-dodecane from 0:3:1 to 8:1.

8. The composition of claim 7, wherein the $C_{12}$ mono-olefins comprise:
   from 10 to 33 wt. % of 1-dodecene; and
   from 2 to 32 wt. % 6-hepten-1-yl-cyclopentane.

9. The composition of claim 7, wherein:
   the $C_{12}$ mono-olefins further comprise from 29 to 88 wt. % non-cyclic branched $C_{12}$ mono-olefins; and
   the non-cyclic branched $C_{12}$ mono-olefins comprise 5-methyl-1-undecene, 7-methyl-1-undecene, 4-ethyl-1-decene, 6-ethyl-1-decene, 3-propyl-1-nonene, 5-propyl-1-nonene, 2-butyl-1-octene, 3-butyl-1-octene, 4-butyl-1-octene, or any combination thereof.

10. The composition of claim 7, wherein:
    the composition comprises from 62 to 97 wt. % $C_{12}$ mono-olefins; and
    the weight ratio of heptylcyclopentane to n-dodecane is from 0.5:1 to 2:1.

11. The composition of claim 10, wherein the $C_{12}$ mono-olefins comprise a weight ratio of 1-dodecene to 6-hepten-1-yl-cyclopentane from 0.9:1 to 6:1.

12. A composition comprising at least 60 wt. % $C_{14}$ mono-olefins, the $C_{14}$ mono-olefins comprising:
    i) at least 12 wt. % 1-tetradecene; and
    ii) at least 0.5 wt. % 8-nonen-1-yl-cyclopentane;
    wherein the composition further comprises a total of from 3 to 30 wt. % of n-tetradecane and nonylcyclopentane.

13. The composition of claim 12, wherein the composition comprises a total of from 5 to 25 wt. % n-tetradecane and nonylcyclopentane.

14. The composition of claim 12, wherein the $C_{14}$ mono-olefins comprise:
    from 16 to 38 wt. % 1-tetradecene; and
    from 2 to 24 wt. % 8-nonen-1-yl-cyclopentane.

15. The composition of claim 12, wherein:
    the $C_{14}$ mono-olefins further comprise from 30 to 80 wt. % non-cyclic branched $C_{14}$ mono-olefins; and
    the non-cyclic branched $C_{14}$ mono-olefins comprise 7-methyl-1-tridecene, 6-ethyl-1-dodecene, 5-propyl-1-undecene, 4-butyl-1-decene, 3-pentyl-1-nonene, or any combination thereof.

16. The composition of claim 12, wherein:
    the composition comprises from 60 to 99 wt. % $C_{14}$ mono-olefins; and
    a weight ratio of 1-tetradecene to 8-nonen-1-yl-cyclopentane is from 1:1 to 10:1.

17. A composition comprising:
    (a) a $C_{10}$ composition comprising at least 55 wt. % $C_{10}$ mono-olefins, the $C_{10}$ mono-olefins comprising:
        i) from 11 to 45 wt. % 1-decene;
        ii) at least 0.5 wt. % 2-butyl-1-hexene;
        iii) at least 1 wt. % 3-propyl-1-heptene;
        iv) from 0.5 to 12 wt. % wt. % 4-ethyl-1-octene;
        v) at least 4 wt. % 4-penten-1-yl-cyclopentane; and
        vi) from 2 to 40 wt. % 5-methyl-1-nonene;
    (b) a $C_{12}$ composition comprising at least 60 wt. % $C_{12}$ mono-olefins, the $C_{12}$ mono-olefins comprising:
        i) at least 8 wt. % 1-dodecene; and
        ii) at least 0.5 wt. % 6-hepten-1-yl-cyclopentane;
        wherein the composition further comprises heptylcyclopentane and n-dodecane at a weight ratio of heptylcyclopentane to n-dodecane from 0:3:1 to 8:1; and (c) a $C_{14}$ composition comprising at least 60 wt. % $C_{14}$ mono-olefins, the $C_{14}$ mono-olefins comprising:
  i) at least 12 wt. % 1-tetradecene; and
  ii) at least 0.5 wt. % 8-nonen-1-yl-cyclopentane;
  wherein the composition further comprises a total of from 3 to 30 wt. % of n-tetradecane and nonylcyclopentane.

18. The composition of claim 17, wherein the composition comprises:
  from 25 to 47 wt. % of the $C_{10}$ composition;
  from 30 to 55 wt. % of the $C_{12}$ composition; and
  from 12 to 35 wt. % of the $C_{14}$ composition.

19. The composition of claim 18, wherein the composition comprises from 75 to 95 wt. % of $C_{10-14}$ mono-olefins.

20. The composition of claim 17, further comprising $C_{16-18}$ hydrocarbons.

21. The composition of claim 20, wherein:
  the composition comprises from 75 to 95 wt. % of $C_{10-18}$ mono-olefins; and
  the composition comprises:
    from 15 to 40 wt. % of the $C_{10}$ composition;
    from 19 to 40 wt. % of the $C_{12}$ composition;
    from 7 to 25 wt. % of the $C_{14}$ composition; and
    from 18 to 40 wt. % of $C_{16-18}$ hydrocarbons.

* * * * *